United States Patent
Murgia et al.

(10) Patent No.: US 8,611,552 B1
(45) Date of Patent: Dec. 17, 2013

(54) DIRECTION-AWARE ACTIVE NOISE CANCELLATION SYSTEM

(75) Inventors: Carlo Murgia, Sunnyvale, CA (US);
Carlos Avendano, Campbell, CA (US);
Jean Laroche, Santa Cruz, CA (US)

(73) Assignee: Audience, Inc., Mountain View, CA (US)

( * ) Notice: Subject to any disclaimer, the term of this patent is extended or adjusted under 35 U.S.C. 154(b) by 398 days.

(21) Appl. No.: 12/868,417

(22) Filed: Aug. 25, 2010

(51) Int. Cl.
*A61F 11/06* (2006.01)

(52) U.S. Cl.
USPC ...... 381/71.14; 381/71.1; 381/71.6; 381/71.8

(58) Field of Classification Search
USPC ............ 381/71.1, 71.6, 74, 92, 71.8, 71.14
See application file for complete search history.

(56) References Cited

U.S. PATENT DOCUMENTS

| | | | |
|---|---|---|---|
| 6,160,265 A * | 12/2000 | Bacchi et al. | 250/559.29 |
| 8,160,265 B2 * | 4/2012 | Mao et al. | 381/74 |
| 8,180,062 B2 * | 5/2012 | Turku et al. | 381/27 |
| 2007/0154031 A1 * | 7/2007 | Avendano et al. | 381/92 |
| 2010/0158267 A1 * | 6/2010 | Thormundsson et al. | 381/92 |
| 2011/0158419 A1 * | 6/2011 | Theverapperuma et al. | 381/71.1 |

* cited by examiner

*Primary Examiner* — Disler Paul
(74) *Attorney, Agent, or Firm* — Carr & Ferrell LLP

(57) ABSTRACT

Robust feedforward active noise cancellation is provided which can overcome or substantially alleviate problems associated with the diverse and dynamic nature of the surrounding acoustic environment. A multi-faceted analysis is performed to determine the direction (or directions) of propagation of noise in the surrounding acoustic environment. The direction of propagation is then utilized to determine direction-dependent characteristics of the acoustic path between a reference position where the noise is captured and a desired position where the noise is to be cancelled. These characteristics are used to form a feedforward signal adapted to cancel the noise at the desired position. By forming the feedforward signal based on direction-dependent characteristics of the acoustic path, the techniques described herein can achieve optimal noise cancellation at the desired location, regardless of the direction of propagation of the noise.

20 Claims, 7 Drawing Sheets

DIRECTION-AWARE ACTIVE NOISE CANCELLATION SYSTEM

BACKGROUND

1. Field of the Invention

The present invention relates generally to audio processing, and more particularly to techniques for active noise cancellation.

2. Description of Related Art

An active noise cancellation (ANC) system in an earphone-based audio device can be used to reduce background noise. The ANC system forms a compensation signal adapted to cancel background noise at a listening position at or near an ear of a user. The compensation signal is provided to an acoustic transducer (e.g. a loudspeaker) which generates an "anti-noise" acoustic wave. The anti-noise acoustic wave is intended to attenuate or eliminate the background noise at the listening position via destructive interference. Consequently, the combination of the anti-noise acoustic wave and the background noise at the listening position results in cancellation of both and hence a reduction in noise.

ANC systems may generally be divided into feedforward ANC systems and feedback ANC systems. In a typical feedforward ANC system, a reference microphone provides a reference signal based on the background noise captured at a reference position. The reference signal is then used by the ANC system to predict the background noise at the listening position so that it can be cancelled. Typically, this prediction utilizes a transfer function which models the acoustic path from the reference position to the listening position. Active noise cancellation is then performed to form a compensation signal adapted to cancel the noise, whereby the reference signal is inverted, weighted and delayed or more generally filtered based on the transfer function.

Errors in feedforward active noise cancellation can occur due to the difficulty in forming a transfer function which accurately models the acoustic path from the reference position to the listening position. Specifically, since the surrounding acoustic environment is rarely fixed, the background noise at the listening position is constantly changing. For example, the location and number of noise sources which form the resultant background noise can change over time. These changes affect the acoustic path from the reference position to the listening position. For example, the propagation delay of the background between the reference position and the listening position depends on the direction (or directions) the background noise is coming from. Similarly, the amplitude difference of the noise at the reference position and at the listening position may be direction dependent.

If the transfer function used to model the acoustic path from the reference position to the listening position is even slightly incorrect, residual noise will remain at the listening position. The residual noise can interfere with the listening experience of desired sound, and is annoying. In some instances, errors in the transfer function may result in the generation of an anti-noise acoustic wave that constructively interferes with the background noise at the listening position. In such a case, the combination of the anti-noise acoustic wave and the background noise may result in an increase in the noise at the listening position, rather than a decrease.

It is therefore desirable to provide active noise cancellation techniques which can increase the quality and robustness of active noise cancellation systems in diverse acoustic environments.

SUMMARY

The present technology provides systems and methods for robust feedforward active noise cancellation which can overcome or substantially alleviate problems associated with the diverse and dynamic nature of the surrounding acoustic environment. The present technology carries out a multi-faceted analysis to determine the direction (or directions) of propagation of noise in the surrounding acoustic environment. The direction of propagation is then utilized to determine direction-dependent characteristics of the acoustic path between a reference position where the noise is captured and a desired position where the noise is to be cancelled. These characteristics are used to form a feedforward signal adapted to cancel the noise at the desired position. By forming the feedforward signal based on direction-dependent characteristics of the acoustic path, the techniques described herein can achieve optimal noise cancellation at the desired location, regardless of the direction of propagation of the noise.

A method for reducing an acoustic energy level at a listening position as described herein includes receiving a primary acoustic wave at a first reference position to form a first reference signal. The primary acoustic wave is also received at a second reference position to form a second reference signal. A direction of propagation of the primary acoustic wave is then determined based on the first and second reference signals. A feedforward signal is formed based on the determined direction of propagation of the primary acoustic wave. A secondary acoustic wave is then generated based on the feedforward signal, the secondary acoustic wave adapted to reduce the acoustic energy level at the listening position.

A system for reducing an acoustic energy level at a listening position as described herein includes a first reference microphone to receive a primary acoustic wave at a first reference position to form a first reference signal. A second reference microphone receives the primary acoustic wave at a second reference position to form a second reference signal. A feedforward module determines a direction of propagation of the primary acoustic wave based on the first and second reference signals. The feedforward module also forms a feedforward signal based on the determined direction of propagation of the primary acoustic wave. An audio transducer generates a secondary acoustic wave based on the feedforward signal, the secondary acoustic wave adapted to reduce the acoustic wave at the listening position.

A computer readable storage medium as described herein has embodied thereon a program executable by a processor to perform a method for reducing an acoustic energy level at a listening position as described above.

Other aspects and advantages of the present invention can be seen on review of the drawings, the detailed description, and the claims which follow.

DETAILED DESCRIPTION

The present technology provides systems and methods for robust feedforward active noise cancellation which can overcome or substantially alleviate problems associated with the diverse and dynamic nature of the surrounding acoustic environment. The present technology carries out a multi-faceted analysis to determine the direction (or directions) of propagation of noise in the surrounding acoustic environment. The direction of propagation is then utilized to determine direction-dependent characteristics of the acoustic path between a reference position where the noise is captured and a desired position where the noise is to be cancelled. These characteristics are used to form a feedforward signal adapted to cancel the noise at the desired position.

By forming the feedforward signal based on direction-dependent characteristics of the acoustic path, the techniques described herein can achieve optimal noise cancellation at the desired location, regardless of the direction of propagation of the noise. In doing so, the feedforward active noise cancellation techniques described herein can increase the quality and robustness of active noise cancellation in diverse acoustic environments.

Embodiments of the present technology may be practiced on any earphone-based audio device that is configured to receive and/or provide audio such as, but not limited to, cellular phones, MP3 players, phone handsets and headsets. While some embodiments of the present technology will be described in reference to operation on a cellular phone, the present technology may be practiced on any audio device.

Figure 1:
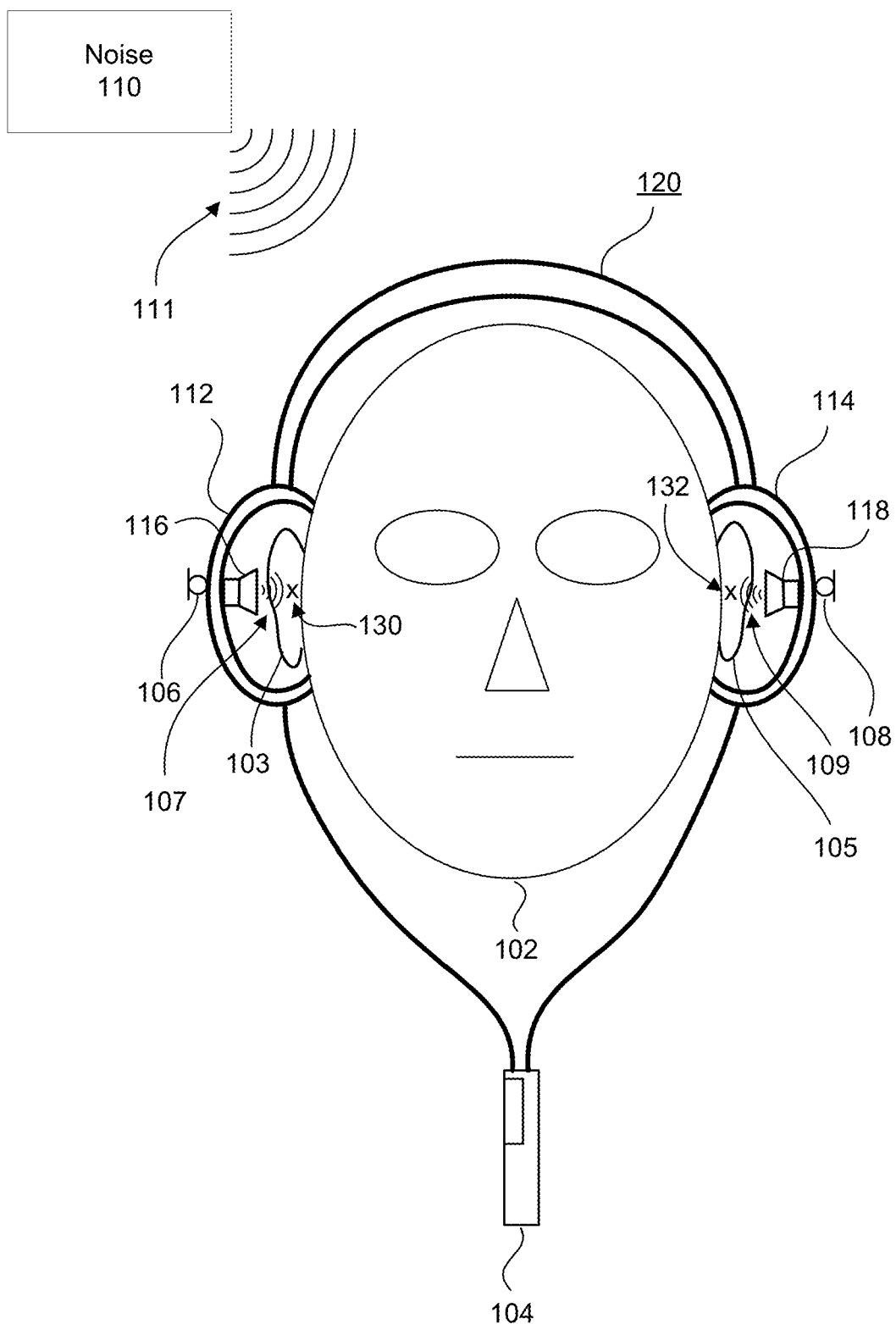
FIG. 1 is an illustration of an environment in which embodiments of the present technology may be used.

FIG. 1 is an illustration of an environment in which embodiments of the present technology may be used. An audio device 104 may act as a source of audio content to a headset 120 which can be worn over or in the ears 103, 105 of a user 102. The audio content provided by the audio device 104 may for example be stored on a storage media such as a memory device, an integrated circuit, a CD, a DVD, etc for playback to the user 102. The audio content provided by the audio device 104 may include a far-end acoustic signal received over a communications network, such as speech of a remote person talking into a second audio device. The audio device 104 may provide the audio content as mono or stereo acoustic signals to the headset 120 via one or more audio outputs. As used herein, the term "acoustic signal" refers to a signal derived from or based on an acoustic wave corresponding to actual sounds, including acoustically derived electrical signals which represent an acoustic wave.

The audio device 104 may be coupled to the headset 120 via one or more wires, a wireless link, or any other mechanism for communication of information. In the illustrated embodiment, the exemplary headset 120 includes a first earpiece 112 positionable on or in the ear 103 of the user 102, and a second earpiece 114 positionable on or in the ear 105 of the user 102. Alternatively, the headset 120 may include a single earpiece. The term "earpiece" as used herein refers to any sound delivery device positionable on or in a person's ear. The term "earpiece" includes an earcup worn on or around a person's ear, as well as an earbud worn within a person's ear.

The first earpiece 112 includes an audio transducer 116 which generates an acoustic wave 107 proximate the ear 103 of the user 102 in response to a first acoustic signal t1(t). The second earpiece 114 includes an audio transducer 118 which generates an acoustic wave 109 proximate the ear 105 of the user 102 in response to a second acoustic signal t2(t). Each of the audio transducers 116, 118 may for example be a loudspeaker, or any other type of audio transducer which generates an acoustic wave in response to an electrical signal.

As described below, in the illustrated embodiment the first acoustic signal t1(t) includes a desired signal s1(t) such as the audio content provided by the audio device 104. The first acoustic signal t1(t) also includes a first feedforward signal f1(t) adapted to cancel undesired background noise at a first listening position 130 using the techniques described herein. Similarly, the second acoustic signal t2(t) includes a desired signal s2(t) such as the audio content provided by the audio device 104. The second acoustic signal t2(t) also includes a second feedforward signal f2(t) adapted to cancel undesired background noise at a second listening position 132 using the techniques described herein. In some alternative embodiments, the desired signals s1(t) and s2(t) may be omitted.

As shown in FIG. 1, an acoustic wave (or waves) 111 will also be generated by noise 110 in the environment surrounding the user 102. Although the noise 110 is shown coming from a single location in FIG. 1, the noise 110 may include any sounds coming from one or more locations that differ from the location of the transducers 116, 118, and may include reverberations and echoes. The noise 110 may be stationary, non-stationary, and/or a combination of both stationary and non-stationary noise.

The total acoustic wave at the first listening position 130 is a superposition of the acoustic wave 107 generated by the transducer 116 and the acoustic wave 111 generated by the noise 110. The first listening position 130 may for example be in front of the eardrum of ear 103, where the user 102 will hear it. As described herein, the portion of the acoustic wave 107 due to the first feedforward signal f1(t) is configured to destructively interfere with the acoustic wave 111 at the first listening position 130. In other words, the combination of the portion of the acoustic wave 107 due to the first feedforward signal f1(t) and the acoustic wave 111 due to the noise 110 at the first listening position 130 results in cancellation of both and hence a reduction in the acoustic energy level of noise at the first listening position 130. As a result, the portion of the acoustic wave 107 due to the desired audio signal s1(t) remains at the first listening position 130, where the user 102 will hear it.

Similarly, the total acoustic wave at the second listening position 132 is a superposition of the acoustic wave 109 generated by the transducer 118 and the acoustic wave 111 generated by the noise 110. The second listening position 132 may for example be in front of the eardrum of the ear 105. As described herein, the portion of the acoustic wave 109 due to the second feedforward signal f2(t) is configured to destructively interfere with the acoustic wave 111 at the second listening position 132. In other words, the combination of the portion of the acoustic wave 109 due to the second feedforward signal f2(t) and the acoustic wave 111 due to the noise 110 at the second listening position 132 results in cancellation of both. As a result, the portion of the acoustic wave 109 due to the desired signal s2(t) remains at the second listening position 132, where the user 102 will hear it.

As shown in FIG. 1, the first earpiece 112 includes a first reference microphone 106 at a first reference position. Similarly, the second earpiece 114 includes a second reference microphone 108 at a second reference position. In some alternative embodiments, the first and second reference microphones 106 and 108 may for example be arranged on the same earpiece. It should be noted that embodiments of the technology described herein may be practiced utilizing only a single earpiece. In some embodiments, more than two reference microphones may be used to perform active noise cancellation described herein.

The acoustic wave 111 due to the noise 110 is picked up by the first reference microphone 106 and by the second reference microphone 108. The signal received by the first reference microphone 106 is referred to herein as the first reference signal $r1(t)$. The signal received by the second reference microphone 108 is referred to herein as the second reference signal $r2(t)$.

As described below, the direction (or directions) of propagation of the acoustic wave (or waves) 111 generated by the noise 110 is derived based on the differences (e.g. energy and/or phase differences) between the first reference signal $r1(t)$ and the second reference signal $r2(t)$. Due to the spatial separation of the first reference microphone 106 and the second reference microphone 108, the first reference signal $r1(t)$ may have an amplitude difference and a phase difference relative to the second reference signal $r2(t)$. These differences can be used to determine the direction (or directions) of propagation of the acoustic wave (or waves) 111, and thus the location(s) of the source of noise 110.

In the illustrated example, the first reference microphone 106 is closer to the noise 110 than the second reference microphone 108, and the second reference microphone 108 is shadowed by the head. As a result, the intensity level of the acoustic wave 111 is higher at the first reference microphone 106 than at the second reference microphone 108, resulting in a larger energy level received by the first reference microphone 106. Further embodiments may use a combination of energy level differences and time delays to determine the location(s) of the noise 110.

In various embodiments, where the first and second reference microphones 106, 108 are omni-directional microphones that are closely-spaced (e.g., 1-2 cm apart), a beamforming technique may be used to simulate a pair of forwards-facing and backwards-facing directional microphones. The level difference between the outputs of this pair of microphones may be used to determine the direction of propagation of the acoustic wave 111, which is used to perform active noise cancellation as described herein.

As described below, the direction of propagation of the acoustic wave 111 is utilized to form a first transfer function which accurately models direction-dependent characteristics of the acoustic path from the reference position of the first reference microphone 106 to the first listening position 130. Active noise cancellation is then performed at the first listening position 130 by forming the first feedforward signal $f1(t)$, whereby the first reference signal $r1(t)$ is inverted, weighted and delayed (or more generally filtered) based on the first transfer function. By forming the first feedforward signal $f1(t)$ based on direction-dependent characteristics of the acoustic path, the techniques described herein can achieve optimal active noise cancellation, regardless of the direction of propagation of the acoustic wave 111.

The direction of propagation of the acoustic wave 111 is also utilized to form a second transfer function which accurately models direction-dependent characteristics of the acoustic path from the reference position of the second reference microphone 108 and the second listening position 132. Active noise cancellation is then performed at the second listening position 132 by forming the second feedforward signal $f2(t)$, whereby the second reference signal $r2(t)$ is inverted, weighted and delayed (or more generally filtered) based on the second transfer function.

Figure 2:
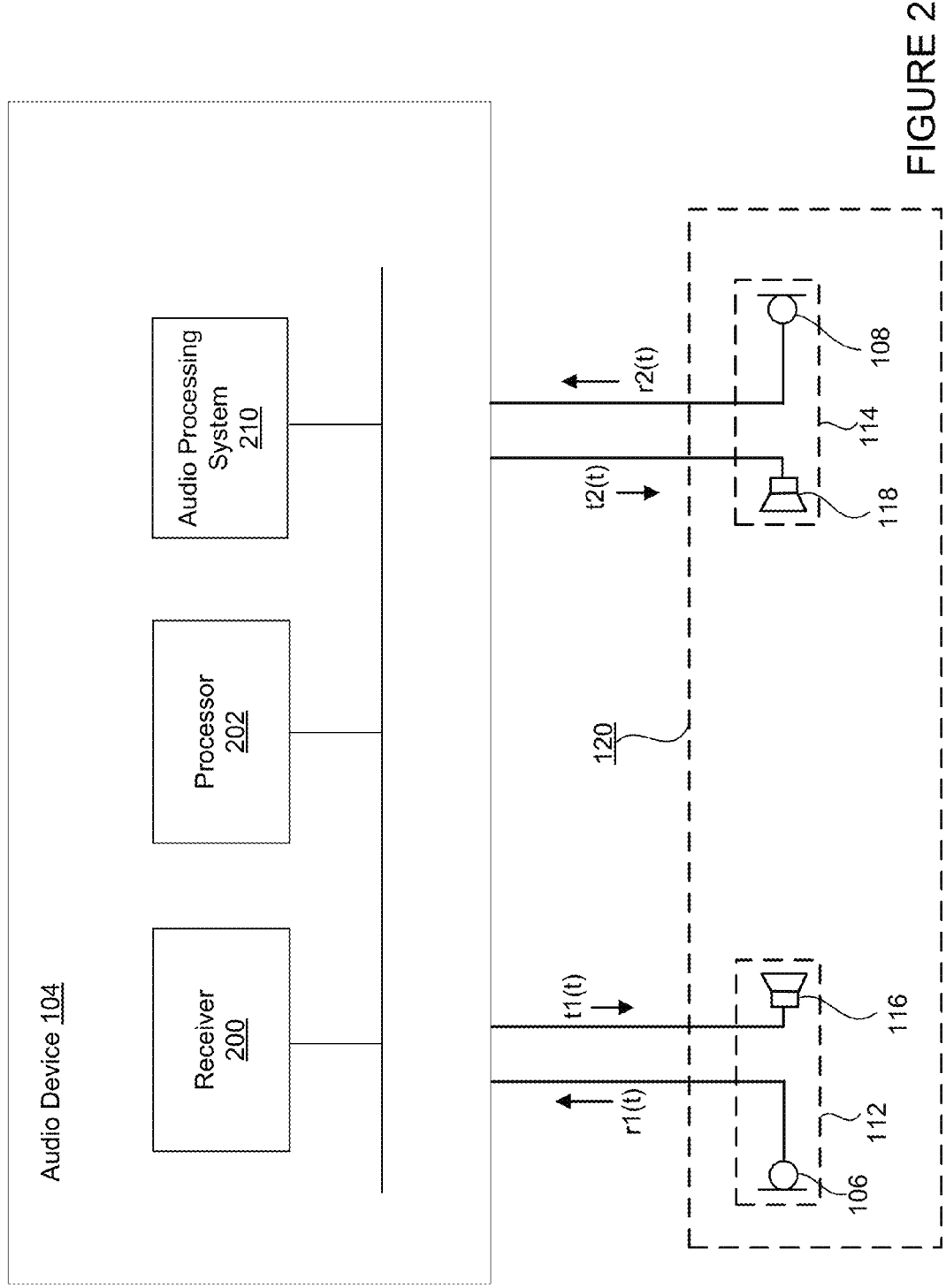
FIG. 2 is a block diagram of an exemplary audio device coupled to an exemplary headset.

FIG. 2 is a block diagram of an exemplary audio device 104 coupled to an exemplary headset 120. In the illustrated embodiment, the audio device 104 includes a receiver 200, a processor 202 and an audio processing system 210. The audio device 104 may further or other components necessary for audio device 104 operations. Similarly, the audio device 104 may include fewer components that perform similar or equivalent functions to those depicted in FIG. 2. In some embodiments, the audio device 104 includes one or more microphones and/or one or more output devices.

Processor 202 may execute instructions and modules stored in a memory (not illustrated in FIG. 2) in the audio device 104 to perform functionality described herein, including active noise cancellation. Processor 202 may include hardware and software implemented as a processing unit, which may process floating operations and other operations for the processor 202.

The exemplary receiver 200 is an acoustic sensor configured to receive a signal from a communications network. In some embodiments, the receiver 200 may comprise an antenna device. The signal may then be forwarded to the audio processing system 210, and provided as audio content to the user 102 via the headset 120 in conjunction with active noise cancellation as described herein. The present technology may be used in one or both of the transmit and receive paths of the audio device 104.

The audio processing system 210 is configured to receive the first reference signal $r1(t)$ from the first reference microphone 106 and the second reference signal $r2(t)$ from the second reference microphone 108, and process the signals. Processing includes performing active noise cancellation as described herein. The audio processing system 210 is discussed in more detail below.

The acoustic signals received by the first reference microphone 106 and the second reference microphone 108 may be converted into electrical signals. The electrical signals may themselves be converted by an analog to digital converter (not shown) into digital signals for processing in accordance with some embodiments.

The audio device 104 may be coupled to the headset 120 via one or more wires, a wireless link, or any other mechanism for communication of information. In the illustrated embodiment, active noise cancellation techniques are carried out by the audio processing system 210 of the audio device 104. Thus, in the illustrated embodiment the audio processing system 210 includes resources to form the first and second feedforward signals $f1(t)$, $f2(t)$ used to perform active noise cancellation. Alternatively, as described in more detail below with regard to FIG. 6, the feedforward signals may be formed utilizing resources embedded within the headset 120 itself.

Figure 3:
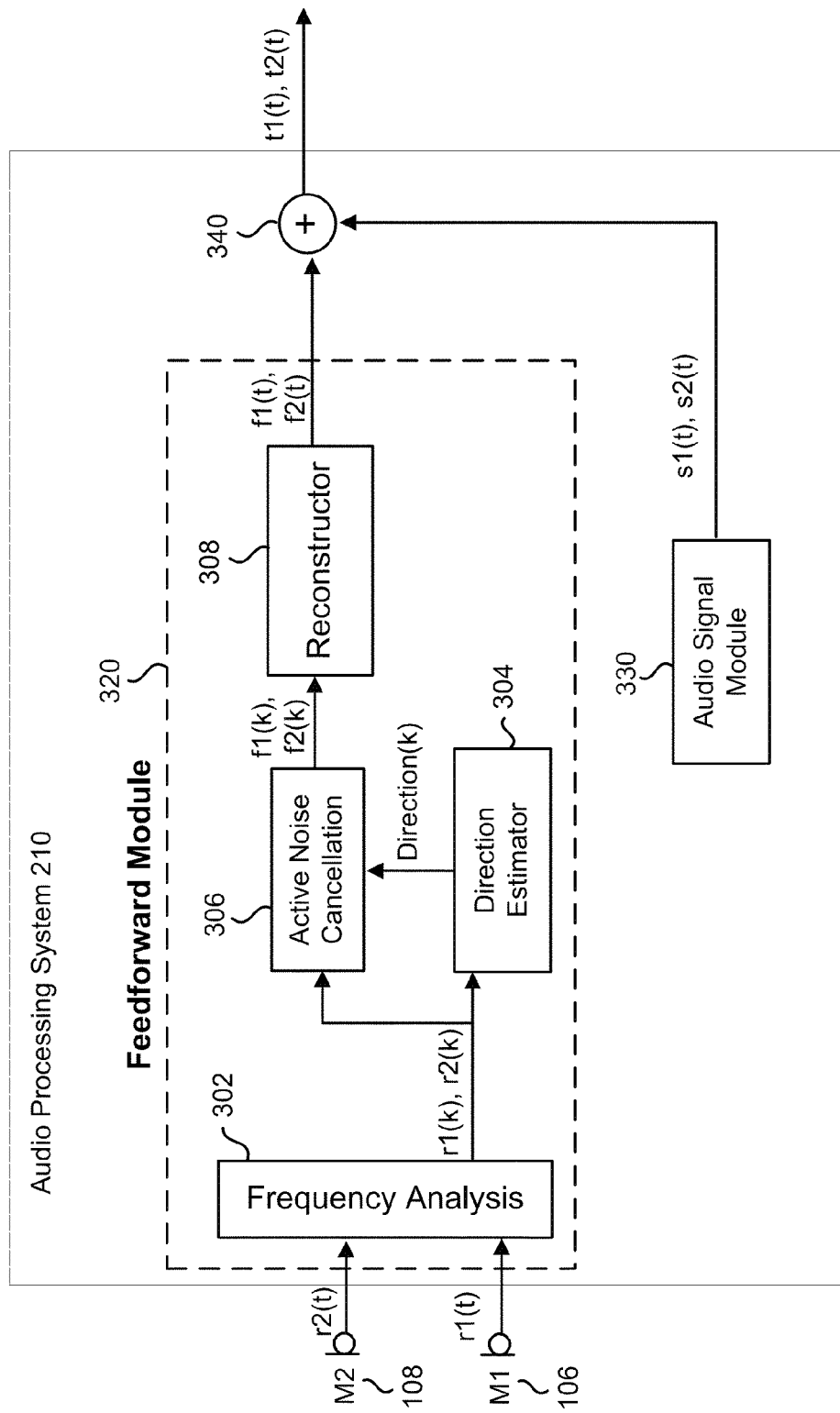
FIG. 3 is a block diagram of an exemplary audio processing system for performing active noise cancellation as described herein.

FIG. 3 is a block diagram of an exemplary audio processing system 210 for performing active noise cancellation as described herein. In exemplary embodiments, the audio processing system 210 is embodied within a memory device within audio device 104.

The audio processing system 210 may include frequency analysis module 302, direction estimator module 304, active noise cancellation (ANC) module 306, reconstructor module 308, summing module 340, and audio signal module 330. Audio processing system 210 may include more or fewer components than those illustrated in FIG. 3, and the functionality of modules may be combined or expanded into fewer or additional modules. Exemplary lines of communication are illustrated between various modules of FIG. 3, and in other figures herein. The lines of communication are not intended to limit which modules are communicatively coupled with others, nor are they intended to limit the number and type of signals communicated between modules.

In operation, the first reference signal r1(t) received from the first reference microphone 106 and the second reference signal r2(t) received from the second reference microphone 108 are converted to electrical signals. The electrical signals are provided to feedforward module 320 and processed through frequency analysis module 302. In one embodiment, the frequency analysis module 302 takes the signals and mimics the frequency analysis of the cochlea (e.g., cochlear domain), simulated by a filter bank, for each time frame. The frequency analysis module 302 separates each of the first reference signal r1(t) and the second reference signal r2(t) into two or more frequency sub-band signals. A sub-band signal is the result of a filtering operation on an input signal, where the bandwidth of the filter is narrower than the bandwidth of the signal received by the frequency analysis module 302. Alternatively, other filters such as short-time Fourier transform (STFT), sub-band filter banks, modulated complex lapped transforms, cochlear models, wavelets, etc., can be used for the analysis and synthesis.

Because most sounds (e.g. acoustic signals) are complex and include more than one frequency, a sub-band analysis on the acoustic signal determines what individual frequencies are present in each sub-band of the complex acoustic signal during a frame (e.g. a predetermined period of time). For example, the length of a frame may be 4 ms, 8 ms, or some other length of time. In some embodiments there may be no frame at all. The results may include sub-band signals in a fast cochlea transform (FCT) domain. The sub-band signals of the first reference signal r1(t) are expressed as r1(k), and the sub-band signals of the second reference signal r2(t) are expressed as r2(k).

The sub-band signals r1(k) and r2(k) are provided from frequency analysis module 302 to direction estimator module 304. The direction estimator module 304 computes a direction of propagation Direction(k) of the acoustic wave 111 on a per sub-band basis.

The sub-band Direction(k) is computed based on differences such as amplitude and/or phase differences between the sub-band signals r1(k) and r2(k) in each sub-band. Due to the spatial separation of the first reference microphone 106 and the second reference microphone 108, the first reference sub-band signals r1(k) may have an amplitude difference and a phase difference relative to the second reference sub-band signals r2(t). For example, if the first reference microphone 106 is closer to the noise 110 than the second reference microphone 108, energy within the first reference sub-band signals r1(k) due to the noise 110 can be higher than that of the second reference sub-band signals r2(k). This difference thus indicates the location of the noise 110 and thus the direction of propagation of the acoustic wave 111 relative to the position of the first and second reference microphones 106, 108.

Similarly, the phase difference of an acoustic wave (of a single frequency $f_{sw}$) incident on the first reference microphone 106 and the second reference microphone 108 is dependent upon the frequency $f_{sw}$ of the acoustic wave, the distance d between the first reference microphone 106 and the second reference microphone 108, and the angle of incidence β of the acoustic wave upon the first and second reference microphones 106, 108. This can be represented mathematically as $\phi = 2\pi f_{sw} d \cos(\beta)/c$, where c is the speed of sound. This phase difference thus indicates location of the noise 110 and thus the direction of propagation of acoustic wave 111 relative to the position of the first and second reference microphones 106, 108.

The direction estimator module 304 may compute frame energy estimations of the sub-band frame signals, sub-band inter-microphone level difference (sub-band ILD(k)), sub-band inter-microphone time differences (sub-band ITD(k)), and inter-microphone phase differences (sub-band IPD(k)) between the first reference sub-band signals r1(k) and the second reference sub-band signals r2(k). In exemplary embodiments, the direction estimator module 304 uses one or more of the sub-band ILD(k), sub-band ITD(k) and sub-band IPD(k) to compute the sub-band Direction(k). The sub-band Direction(k) can change over time, and may vary from one frame to the next.

Determining energy levels and ILDs is discussed in more detail in U.S. patent application Ser. No. 11/343,524, entitled "System and Method for Utilizing Inter-Microphone Level Differences for Speech Enhancement", and U.S. patent application Ser. No. 12/832,920, entitled "Multi-Microphone Robust Noise Suppression", the disclosures of which each are incorporated by reference.

In the illustrated embodiment, the sub-band Direction(k) is computed based on differences between the sub-band signals r1(k) and r2(k) for that sub-band k. As a result, the sub-band Direction(k) can change over time, and may vary from one frame to the next. As described below, the sub-band Direction (k) is used by the active noise cancellation module 306 to form the first and second feedforward signals f1(t), f2(t).

The sub-band Direction(k) can also vary with sub-band index k within a particular time frame. This may occur, for example, when the acoustic wave 111 is a superposition of two or more acoustic waves which are generated by noise sources at different locations. For example, a first set of one or more of the sub-band signals r1(k), r2(k) correspond to a first acoustic wave from a first noise source at a first location, while a second set of one or more of the sub-band signals r1(k), r2(k) may correspond to a second acoustic wave from a second noise source at a second location. In such a case, the sub-band Direction(k) of the first set of sub-band signals r1(k), r2(k) indicates the direction of propagation of the first acoustic wave. Similarly, the sub-band Direction(k) of the second set of sub-band signals r1(k), r2(k) indicates the direction of propagation of the first acoustic wave. These different sub-band Direction(k) can then be used to perform active noise cancellation of each of the acoustic waves using the techniques described herein. As a result, the contributions of each of the superimposed acoustic waves which form the acoustic wave 111 can be individually cancelled, thereby achieving optimal noise cancellation at the desired location, regardless of the number and directions of propagation the acoustic waves.

The active noise cancellation module 306 receives the sub-band Direction(k) and the sub-band signals r1(k), r2(k). The active noise cancellation module 306 computes a sub-band transfer function d1(k) which models the acoustic path from the location of the first reference microphone 106 to the first listening position 130 based on the sub-band Direction(k) for that sub-band. The sub-band transfer function d1(k) incorporates direction-dependent characteristics of the acoustic path, such as one or more of an amplitude, phase shift and time delay from the first reference microphone 106 to the first listening position 130 as a function of sub-band Direction(k). The transfer function d1(k) can also model the first reference microphone 106 response, the transducer 116 response, and the acoustic path from the transducer 116 to the first listening position 130.

The transfer function d1(k) is then applied to the first reference sub-band signals r1(k) to form first feedforward sub-band signals f1(k) adapted to cancel the acoustic wave 111 at the first listening position 130.

The active noise cancellation module 306 also computes a sub-band transfer function d2(k) which models the acoustic path from the location of the second reference microphone 108 to the second listening position 132 based on the sub-band Direction(k) for that sub-band. The sub-band transfer function d2(k) incorporates direction-dependent characteristics of the acoustic path, such as one or more of an amplitude, phase shift and time delay from the second reference microphone 108 to the second listening position 132 as a function of sub-band Direction(k). The transfer function d2(k) can also model the second reference microphone 108 response, the transducer 118 response, and the acoustic path from the transducer 118 to the second reference position 130.

The transfer function d2(k) is then applied to the second reference sub-band signals r2(k) to from second feedforward sub-band signals f2(k) adapted to cancel the acoustic wave 111 at the second listening position 132.

The parameter values of the transfer functions d1(k), d2(k) as a function of sub-band Direction(k) may for example be determined empirically through calibration. The parameter values may for example be stored in the form of a look-up table in the memory within the audio device 104. As another example, the parameter values may be stored in the form of an approximate function derived based on the calibration measurements.

The first feedforward sub-band signals f1(k) and the second feedforward sub-band signals f2(k) are provided to reconstructor module 308. The reconstructor module 308 performs an inverse transform which converts the first feedforward sub-band signals f1(k) into the time domain to form the first feedforward signal f1(t). The reconstructor module 308 also converts the second feedforward sub-band signals f2(k) into the time domain to form the second feedforward signal f2(t). In the illustrated embodiment, the first and second feedforward sub-band signals f1(k), f2(k) are in the cochlea domain, and thus the reconstructor module 308 performs a transformation from the cochlea domain into the time domain. The conversion may include adding the sub-band signals and may further include applying gains and/or phase shifts to the sub-band signals prior to the addition. The first feedforward signal f1(t) and the second feedforward signal f2(t) are provided to summing module 340.

As shown in FIG. 2, the audio processing system 210 includes an audio signal module 330. The audio signal module 330 provides desired audio content in the form of desired audio signal s1(t) and desired audio signal s2(t). The audio content may be retrieved for example from data stored on a storage media such as a memory device, an integrated circuit, a CD, a DVD etc for playback to the user 102. The audio content may include a far-end acoustic signal received over a communications network, such as speech of a remote person talking into a second audio device. The desired audio signals s1(t) and s2(t) may be provided as mono or stereo signals.

An example of the audio signal module 330 in some embodiments is disclosed in U.S. patent application Ser. No. 12/832,920 filed on Jul. 8, 2010 and entitled "Multi-Microphone Robust Noise Suppression", which is incorporated herein by reference.

The summing module 340 adds the first feedforward signal f1(t) to the desired audio signal s1(t) to form the first acoustic signal t1(t). The summing module 340 adds the second feedforward signal f2(t) to the desired audio signal s2(t) to form the second acoustic signal t2(t). The first acoustic signal t1(t) can then be provided to the first earpiece 112 of the headset 120 to perform active noise cancellation at the first listening position 130. Similarly, the second acoustic signal t2(t) can then be provided to the second earpiece 114 of the headset to perform active noise cancellation at the second listening position 132.

In the illustrated embodiment the first and second acoustic signals t1(t), t2(t) are formed by addition in the time-domain. In some embodiments in which the desired audio signals are processed in the transform domain, the addition may take place in the transform domain, and the results then transformed into the time domain to form the first and second acoustic signals t1(t), t2(t).

Figure 4:
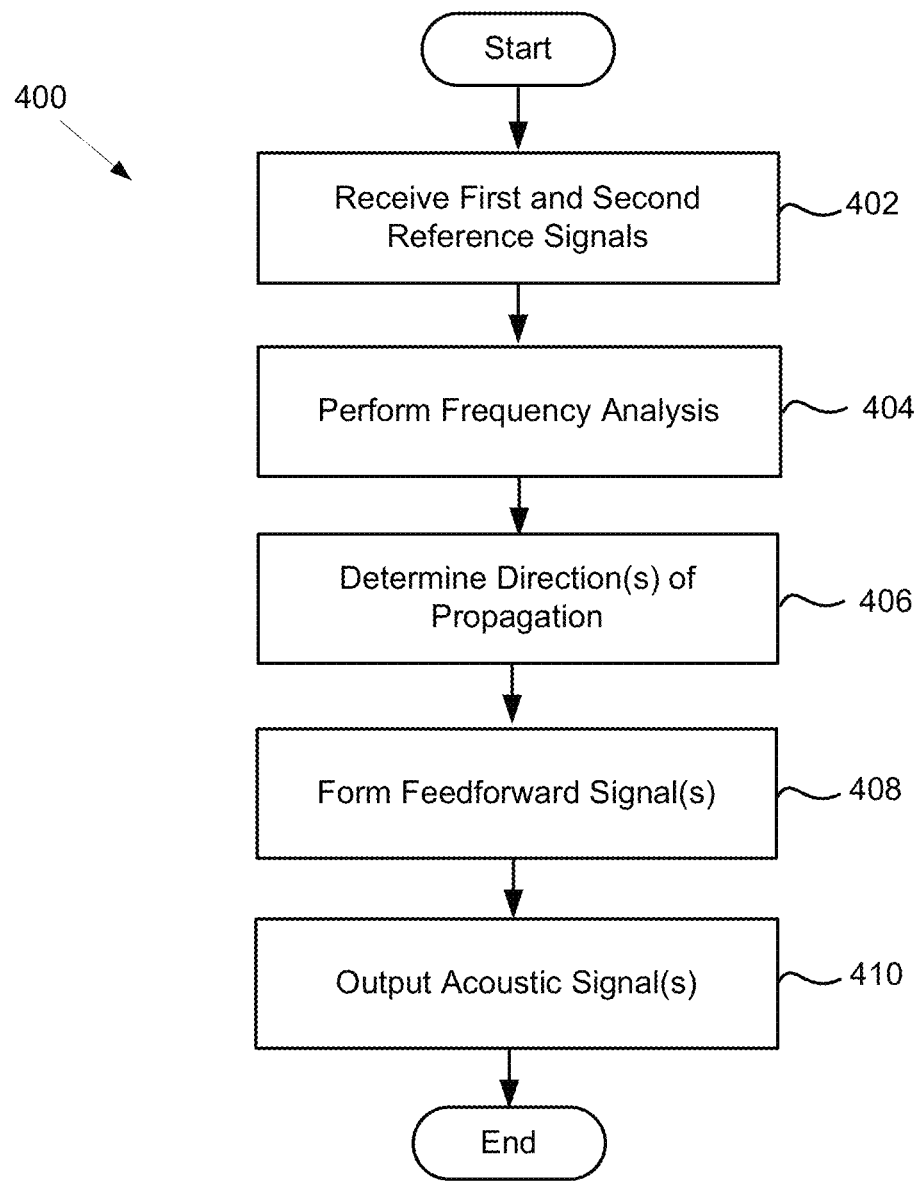
FIG. 4 is a flow chart of an exemplary method for performing active noise cancellation.

FIG. 4 is a flow chart of an exemplary method 400 for performing active noise cancellation. As with all flow charts herein, in some embodiments the steps may be combined, performed in parallel, or performed in a different order. The method 400 of FIG. 4 may also include addition or fewer steps than those illustrated.

In step 402, the first reference signal r1(t) is received by the first reference microphone 106 and the second reference signal r2(t) is received by the second reference microphone 108. In exemplary embodiments, the first and second reference signals r1(t) and r2(t) are converted to digital format for processing. In some embodiments, more than two reference signals may be received and processed.

In step 404, frequency analysis is performed on the first reference signal r1(t) and the second reference signal r2(t). The frequency analysis transforms the first reference signal r1(t) into a transform domain representation given by the first reference sub-band signals r1(k). Similarly, the second reference signal r2(t) is transformed into the second reference sub-band signals r2(k). The sub-band signals may for example be in the fast cochlea transform (FCT) domain, or as another example in the fast Fourier transform (FFT) domain. Other transform domain representations may alternatively be used.

In step 406, the direction(s) of propagation (the sub-band Direction(k)) of the acoustic wave 111 to be cancelled is computed based on differences between the sub-band signals r1(k) and r2(k) in each sub-band. In the illustrated example, the sub-band Direction(k) is determined based on the sub-band ILD(k) in each sub-band. Alternatively, other techniques may be used to determine the sub-band Direction(k).

In step 408, the first feedforward signal f1(t) and the second feedforward signal f2(t) are formed based on the sub-band Direction(k). In the illustrated embodiments, sub-band transfer functions d1(k) and d2(k) are computed utilizing the sub-band Direction(k) for that sub-band. The sub-band transfer function d1(k) is then applied to the first reference sub-band signals r1(k) to form first feedforward sub-band signals f1(k) adapted to cancel the acoustic wave 111 at the first listening position 130. Similarly, the transfer function d2(k) is applied to the second reference sub-band signals r2(k) to form second feedforward sub-band signals f2(k) adapted to cancel the acoustic wave 111 at the second listening position 132. The first and second feedforward sub-band signals f1(k) and f2(k) are then transformed into the time-domain to form first and second feedforward signals f1(t) and f2(t).

In step 410, the first feedforward signal f1(t) is combined with the signal s1(t) to form the first acoustic signal t1(t). The second feedforward signal f2(t) is combined with the signal s2(t) to form the second acoustic signal t2(t). The first acoustic signal t1(t) can then be output to the first earpiece 112 of the headset 120 to perform active noise cancellation at the first listening position 130. The second acoustic signal t2(t) can then be output to the second earpiece 114 of the headset to perform active noise cancellation at the second listening position 132.

Figure 5:
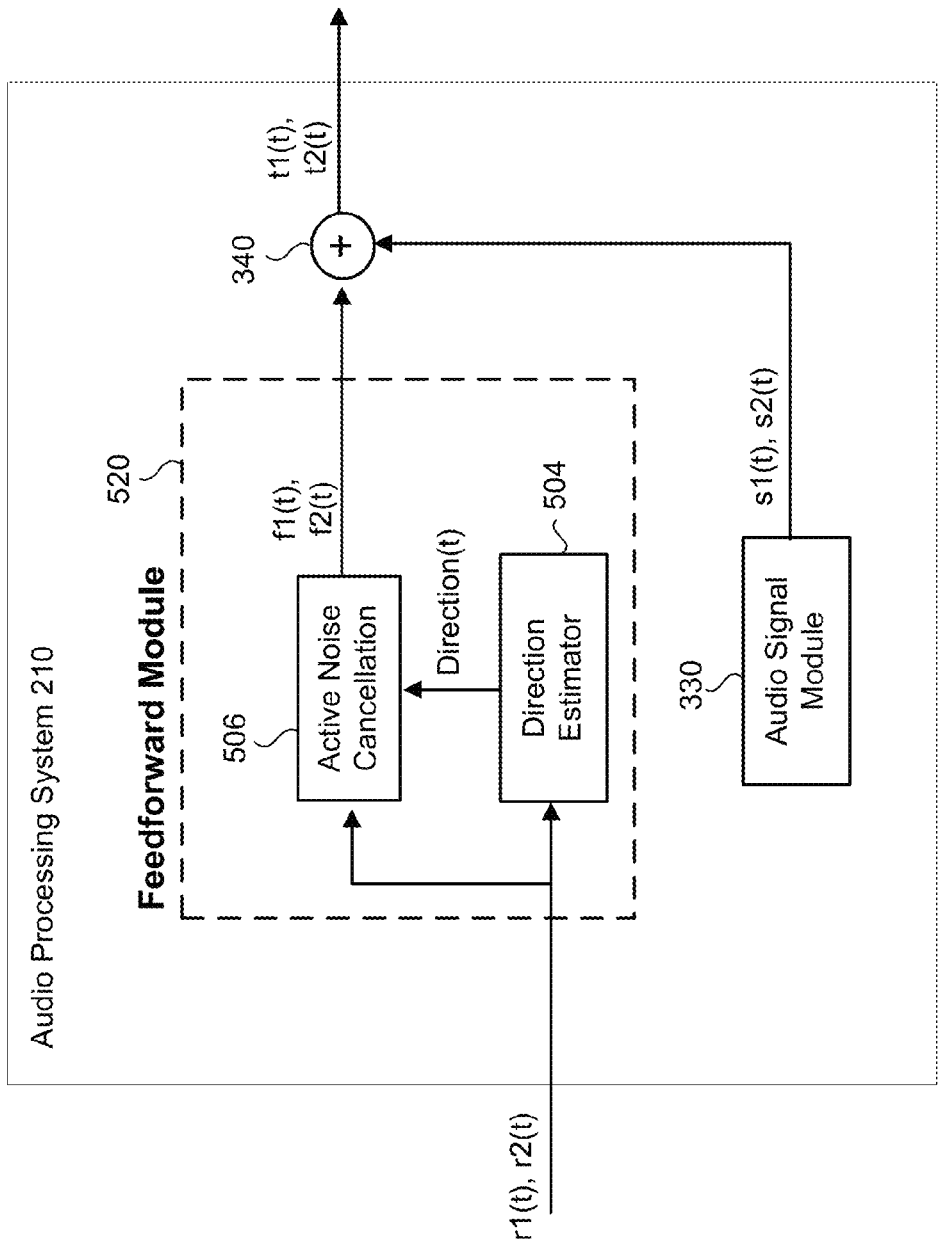
FIG. 5 is a second block diagram of an exemplary audio processing system for performing active noise cancellation as described herein.

FIG. 5 is a second block diagram of an exemplary audio processing system 210 for performing active noise cancellation as described herein. In FIG. 5, the determination of the direction of propagation of the acoustic wave 111 and the formation of the feedforward signals are done in the time domain.

The audio processing system 210 may include direction estimator module 504, active noise cancellation (ANC) module 506, summing module 340, and audio signal module 330. Audio processing system 210 may include more or fewer components than those illustrated in FIG. 5, and the functionality of modules may be combined or expanded into fewer or additional modules.

The first and second reference signals $r1(t)$ and $r2(t)$ are provided to direction estimator module 504 in feedforward module 520. The direction estimator module 504 computes a direction of propagation Direction(t) of the acoustic wave 111 based on a difference between the first and second reference signals $r1(t)$ and $r2(t)$. In the illustrated embodiment, the direction of propagation Direction(t) is determined based on a maximum of the cross-correlation between the first reference signal $r1(t)$ and the second reference signal $r2(t)$. A maximum of the cross-correlation between the first and second reference signals $r1(t)$ and $r2(t)$ indicates the time delay $\tau$ between the arrival of the acoustic wave 111 at the first reference microphone 106 and at the second reference microphone 108. The time delay $\tau$ is dependent upon the distance d between the first reference microphone 106 and the second reference microphone 108, and the angle of incidence $\beta$ of the acoustic wave 111 upon the first and second reference microphones 106, 108. For a known d, this time delay $\tau$ thus indicates the angle of incidence $\beta$, and hence the direction of propagation Direction(t) of the acoustic wave 111. Other techniques for determining the time delay may alternatively be used.

The active noise cancellation module 506 receives the Direction(t) and the first and second reference signals $r1(t)$, $r2(t)$.

The active noise cancellation module 506 computes a transfer function $d1(t)$ which models the acoustic path from the location of the first reference microphone 106 to the first listening position 130 based on the Direction(t). The transfer function $d1(t)$ incorporates direction-dependent characteristics of the acoustic path, such as one or more of an amplitude, phase shift and time delay from the first reference microphone 106 to the first listening position 130 as a function of Direction(t). The transfer function $d1(t)$ can also model the first reference microphone 106 response, the transducer 116 response, and the acoustic path from the transducer 116 to the first listening position 130.

The transfer function $d1(t)$ is then applied to the first reference signal $r1(t)$ to form first feedforward signal $f1(t)$ adapted to cancel the acoustic wave 111 at the first listening position 130.

The active noise cancellation module 306 also computes a transfer function $d2(t)$ which models the acoustic path from the location of the second reference microphone 108 to the second listening position 132 based on the Direction(t). The transfer function $d2(t)$ incorporates direction-dependent characteristics of the acoustic path, such as one or more of an amplitude, phase shift and time delay from the second reference microphone 108 to the second listening position 132 as a function of Direction(t). The transfer function $d2(t)$ can also model the second reference microphone 108 response, the transducer 118 response, and the acoustic path from the transducer 118 to the second listening position 132.

The transfer function $d2(t)$ is then applied to the second reference signal $r2(t)$ to form second feedforward signal $f2(t)$ adapted to cancel the acoustic wave 111 at the second listening position 132.

The parameter values of the transfer functions $d1(t)$, $d2(t)$ as a function of Direction(t) may for example be determined empirically through calibration. The parameter values may for example be stored in the form of a look-up table in the memory within the audio device 104. As another example, the parameter values may be stored in the form of a derived approximate function based on the calibration measurements.

The summing module 340 adds the first feedforward signal $f1(t)$ to the signal $s1(t)$ to form the first acoustic signal $t1(t)$. The summing module 340 adds the second feedforward signal $f2(t)$ to the signal $s2(t)$ to form the second acoustic signal $t2(t)$. The first acoustic signal $t1(t)$ can then be provided to the first earpiece 112 of the headset 120 to perform active noise cancellation at the first listening position 130. The second acoustic signal $t2(t)$ can then be provided to the second earpiece 114 of the headset to perform active noise cancellation at the second listening position 132.

Figure 6:
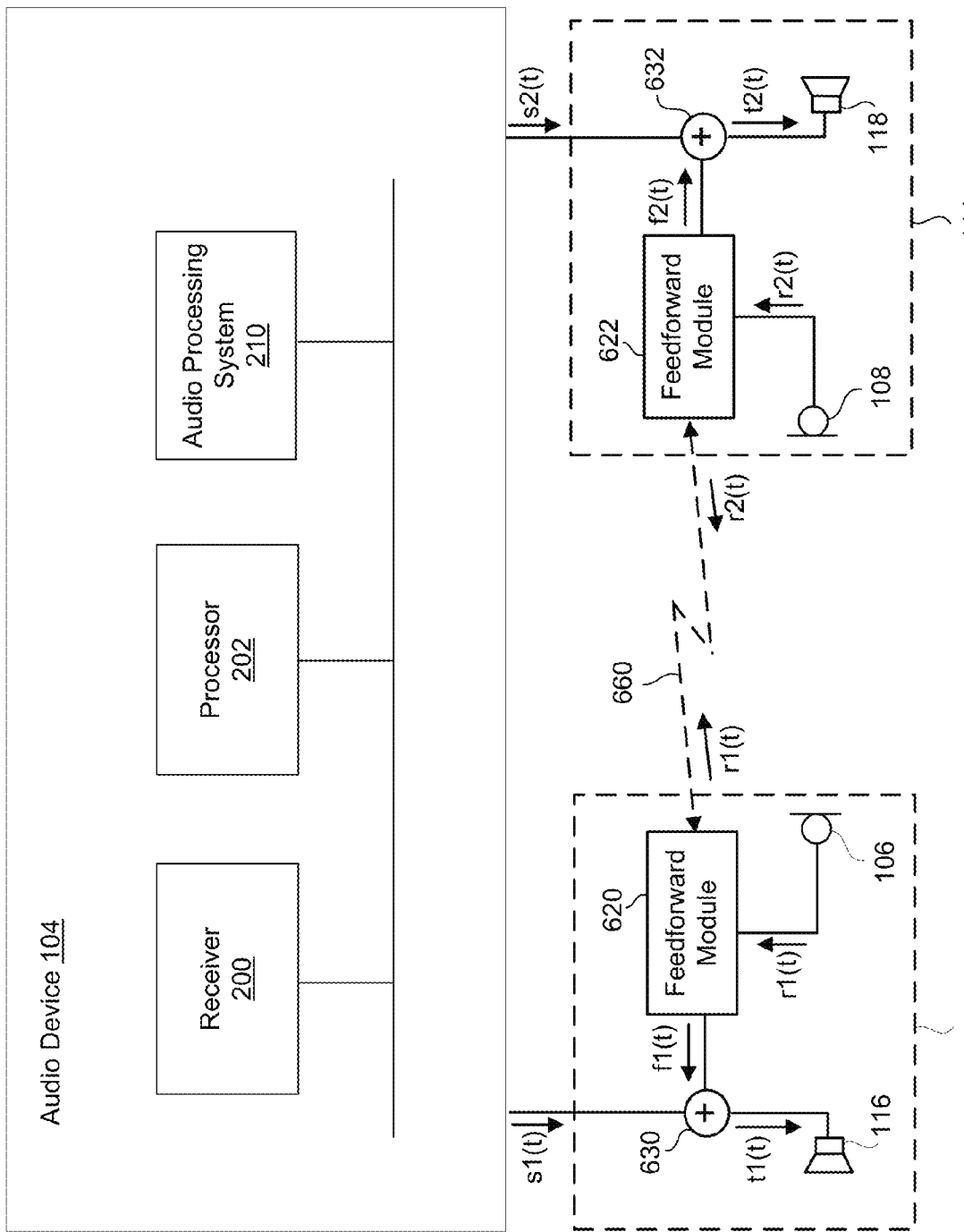
FIG. 6 is a second block diagram of an exemplary audio device coupled an exemplary headset.

FIG. 6 is a second block diagram of an exemplary audio device 104 coupled an exemplary headset 120. In FIG. 6, the active noise cancellation technology described herein is performed by resources embedded within the headset 120 itself.

As shown in FIG. 6, the first earpiece 112 includes a feedforward module 620 and a summing module 630. Similarly, the second earpiece 114 includes a feedforward module 622 and a summing module 632. The first earpiece 112 is coupled to the second earpiece 114 via a communication medium 660. The communication medium 660 may comprise one or more wires, a wireless link, or any other mechanism for communication of data.

As shown in FIG. 6, the feedforward module 622 transmits the second reference signal $r2(t)$ to the feedforward module 620 via the communication medium 660. The feedforward module 620 then forms the first feedforward signal $f1(t)$ based on the first and second reference signals $r1(t)$, $r2(t)$ using the techniques described herein. The summing module 630 adds the first feedforward signal $f1(t)$ to the signal $s1(t)$ provided by the audio device 104 to form the first acoustic signal $t1(t)$. The first acoustic signal $t1(t)$ can then be provided to the audio transducer 116 of the first earpiece 112 to perform active noise cancellation at the first listening position 130 as described herein.

The feedforward module 620 also transmits the first reference signal $r1(t)$ to the feedforward module 622 via the communication medium 660. The feedforward module 622 then forms the second feedforward signal $f2(t)$ using the techniques described herein. The summing module 632 adds the first feedforward signal $f2(t)$ to the signal $s2(t)$ to form the second acoustic signal $t2(t)$. The first acoustic signal $t2(t)$ can then be provided to the audio transducer 118 of the second earpiece 114 to perform active noise cancellation at the second listening position 132 as described herein.

Figure 7:
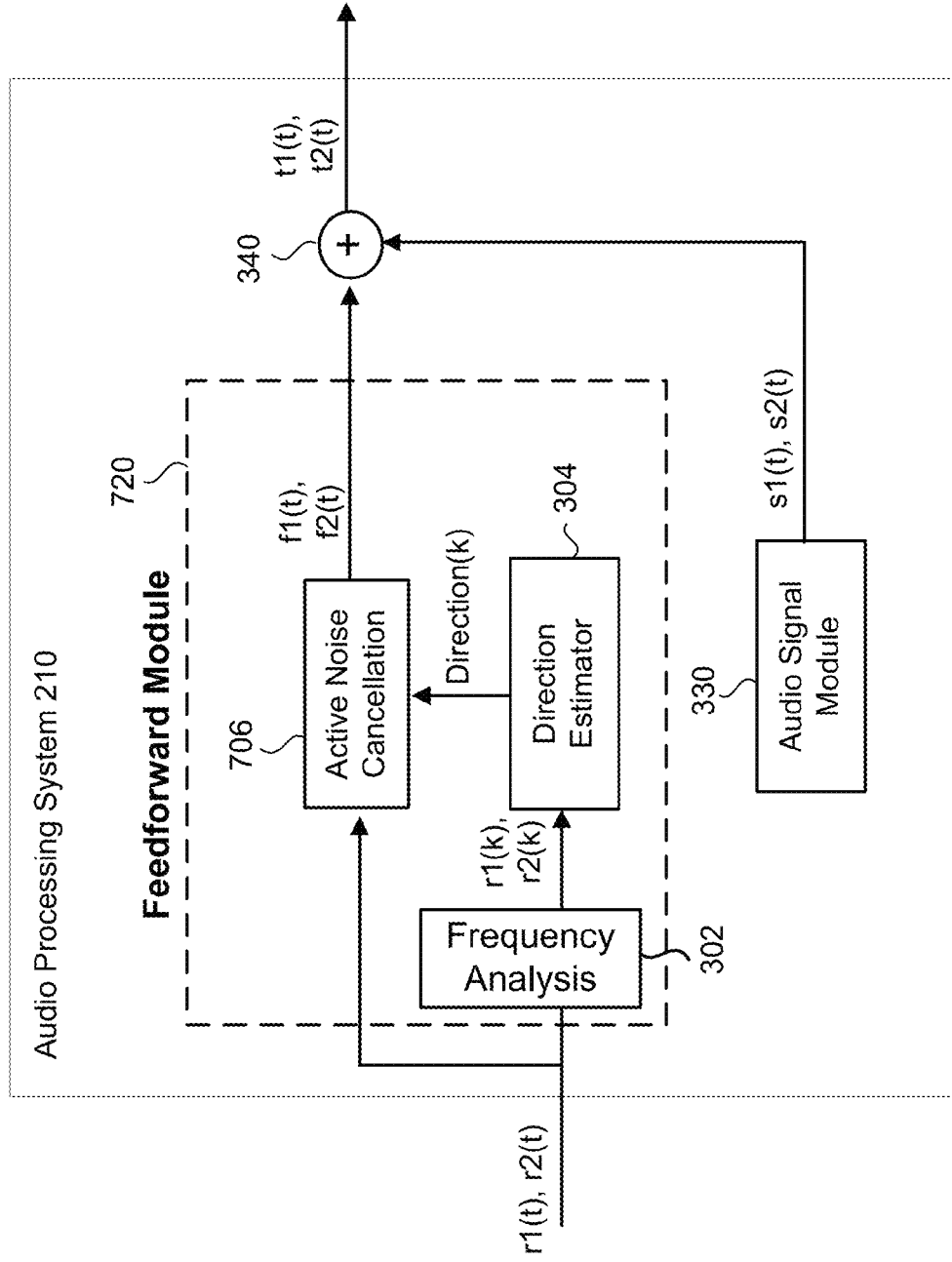
FIG. 7 is a third block diagram of an exemplary audio processing system for performing active noise cancellation as described herein.

FIG. 7 is a third block diagram of an exemplary audio processing system 210 for performing active noise cancellation as described herein. In FIG. 7, the determination of the direction of propagation of the acoustic wave 111 is done in the transform domain, and the formation of the feedforward signals are done in the time domain.

The audio processing system 210 may include feedforward module 720 (which in turn includes frequency analysis module 302, direction estimator module 304, and active noise cancellation (ANC) module 706), summing module 340, and audio signal module 330. Audio processing system 210 may include more or fewer components than those illustrated in FIG. 7, and the functionality of modules may be combined or expanded into fewer or additional modules.

The active noise cancellation module 706 receives the Direction(k) and the first and second reference signals r1(t), r2(t).

The active noise cancellation module 706 computes a transfer function x1(t) which models the acoustic path from the location of the first reference microphone 106 to the first listening position 130 based on the Direction(k). The transfer function x1(t) incorporates direction-dependent characteristics of the acoustic path, such as one or more of an amplitude, phase shift and time delay from the first reference microphone 106 to the first listening position 130 as a function of Direction(k). The transfer function x1(t) can also model the first reference microphone 106 response, the transducer 116 response, and the acoustic path from the transducer 116 to the first listening position 130.

The transfer function x1(t) is then applied to the first reference signal r1(t) to form first feedforward signal f1(t) adapted to cancel the acoustic wave 111 at the first listening position 130.

The active noise cancellation module 706 also computes a transfer function x2(t) which models the acoustic path from the location of the second reference microphone 108 to the second listening position 132 based on the Direction(k). The transfer function x2(t) incorporates direction-dependent characteristics of the acoustic path, such as one or more of an amplitude, phase shift and time delay from the second reference microphone 108 to the second listening position 132 as a function of Direction(t). The transfer function x2(t) can also model the second reference microphone 108 response, the transducer 118 response, and the acoustic path from the transducer 118 to the second listening position 132.

The transfer function x2(t) is then applied to the second reference signal r2(t) to form second feedforward signal f2(t) adapted to cancel the acoustic wave 111 at the second listening position 132.

The parameter values of the transfer functions x1(t), x2(t) as a function of Direction(k) may for example be determined empirically through calibration. The parameter values may for example be stored in the form of a look-up table in the memory within the audio device 104. As another example, the parameter values may be stored in the form of a derived approximate function based on the calibration measurements.

The embodiment illustrated FIG. 7 may provide a number of advantages. First, determining the direction of propagation Direction(k) of the acoustic wave 111 on a per sub-band basis can be more robust than time-domain based techniques. Second, implementing the active noise cancellation module 706 in the time domain can result in less latency than algorithms which include transform-domain analysis and reconstruction.

The above described modules may be comprised of instructions that are stored in a storage media such as a machine readable medium (e.g., computer readable medium). These instructions may be retrieved and executed by a processor. Some examples of instructions include software, program code, and firmware. Some examples of storage media comprise memory devices and integrated circuits. The instructions are operational.

While the present invention is disclosed by reference to the preferred embodiments and examples detailed above, it is to be understood that these examples are intended in an illustrative rather than a limiting sense. It is contemplated that modifications and combinations will readily occur to those skilled in the art, which modifications and combinations will be within the spirit of the invention and the scope of the following claims.

What is claimed is:

1. A method for reducing an acoustic energy level at a listening position, the method comprising:
    receiving a primary acoustic wave at a first reference position to form a first reference signal;
    receiving the primary acoustic wave at a second reference position to form a second reference signal;
    separating each of the first reference signal and the second reference signal into a plurality of sub-band signals in the frequency domain;
    determining, in the frequency domain, a direction of propagation of the primary acoustic wave for each sub-band of the first reference sub-band signal and each sub-band of the second reference sub-band signal based on the first and second reference sub-band signals;
    forming, in the frequency domain, a feedforward sub-band signal based on the determined direction of propagation of the primary acoustic wave; and
    generating a secondary acoustic wave based on the feedforward sub-band signal, the secondary acoustic wave adapted to reduce the acoustic energy level at the listening position.

2. The method of claim 1, wherein determining, in the frequency domain, the direction of propagation of the primary acoustic wave is based on at least one of an amplitude difference and a phase difference between the first reference sub-band signal and the second reference sub-band signal.

3. The method of claim 1, wherein determining, in the frequency domain, the direction of propagation of the primary acoustic wave is based on a time delay estimation between the first reference sub-band signal and the second reference sub-band signal.

4. The method of claim 1, wherein:
    the primary acoustic wave is received at the first reference position by a first reference microphone;
    the secondary acoustic wave is received at the second reference position by a second reference microphone; and
    the secondary acoustic wave is generated by an audio transducer proximate the listening position.

5. The method of claim 4, wherein:
    the first reference microphone is arranged on a first earpiece of a headset;
    the second reference microphone is arranged on a second earpiece of the headset;
    the audio transducer is arranged within the first earpiece of the headset; and
    the listening position is proximate the first earpiece of the headset.

6. The method of claim 5, further comprising:
    forming a second feedforward sub-band signal based on the determined direction of propagation of the primary acoustic wave; and
    generating a tertiary acoustic wave based on the second feedforward sub-band signal via a second audio transducer arranged within the second earpiece, the tertiary acoustic wave adapted to reduce an acoustic energy level at a second listening position proximate the second earpiece.

7. The method of claim 1, wherein determining, in the frequency domain, the direction of propagation of the primary acoustic wave comprises determining a location of an acoustic source of the primary acoustic wave, and the feedforward sub-band signal is formed based on the determined location of the acoustic source.

8. The method of claim 1, wherein:
the primary acoustic wave comprises a plurality of frequency sub-band acoustic waves from a plurality of acoustic sources;
determining, in the frequency domain, the direction of propagation of the primary acoustic wave comprises determining a direction of propagation of each of the plurality of frequency sub-band acoustic waves based on corresponding portions of the first and second reference sub-band signals;
forming the feedforward sub-band signal comprises forming a plurality of frequency sub-band feedforward signals based on the determined direction of propagation of each of the plurality of frequency sub-band acoustic waves; and
generating the secondary acoustic wave is based on the plurality of frequency sub-band feedforward signals.

9. The method of claim 1, wherein the feedforward sub-band signal is further based on estimated sub-band transfer functions between the listening position and the first and second reference positions, the estimated sub-band transfer functions having corresponding parameters at least comprising an amplitude, at least one of the corresponding parameters being determined as a function of the direction of propagation for each sub-band of the primary acoustic wave.

10. A system for reducing an acoustic energy level at a listening position, the system comprising:
a first reference microphone for receiving a primary acoustic wave at a first reference position to form a first reference signal, receiving the primary acoustic wave comprising converting the primary acoustic wave to a frequency-domain such that the first reference signal is separated into sub-bands in the frequency domain;
a second reference microphone for receiving the primary acoustic wave at a second reference position to form a second reference signal, receiving the primary acoustic wave comprising converting the primary acoustic wave to a frequency-domain such that the second reference signal is separated into sub-bands in the frequency domain;
a feedforward module for determining, in the frequency domain, a direction of propagation of the primary acoustic wave for each sub-band of the first reference signal and each sub-band of the second reference signal based on the first and second reference signals, and to form, in the frequency domain, a feedforward sub-band signal based on the determined direction of propagation of the primary acoustic wave; and
an audio transducer for generating a secondary acoustic wave based on the feedforward sub-band signal, the secondary acoustic wave adapted to reduce the acoustic energy level at the listening position.

11. The system of claim 10, wherein the feedforward module determines, in the frequency domain, the direction of propagation of the primary acoustic wave based on at least one of an amplitude and a phase difference between the first reference signal and the second reference signal.

12. The system of claim 10, wherein the feedforward module determines, in the frequency domain, the direction of propagation of the primary acoustic wave based on a time delay estimation between the first reference signal and the second reference signal.

13. The system of claim 10, wherein:
the first reference microphone is arranged on a first earpiece of a headset;
the second reference microphone is arranged on a second earpiece of the headset;
the audio transducer is arranged within the first earpiece of the headset; and
the listening position is proximate the first earpiece of the headset.

14. The system of claim 13, wherein the feedforward module further forms a second feedforward signal based on the determined direction of propagation of the primary acoustic wave, and further comprising a second audio transducer to generate a tertiary acoustic wave based on the second feedforward signal, the tertiary acoustic wave adapted to reduce the energy level at a second listening position proximate the second earpiece.

15. The system of claim 10, wherein the feedforward module determines, in the frequency domain, the direction of propagation by determining a location of an acoustic source of the primary acoustic wave, and the feedforward sub-band signal is formed based on the determined location of the acoustic source.

16. The system of claim 10, wherein:
the primary acoustic wave comprises a plurality of frequency sub-band acoustic waves from a plurality of acoustic sources;
the feedforward module determines, in the frequency domain, the direction of propagation by determining a direction of propagation of each of the plurality of frequency sub-band acoustic waves based on corresponding portions of the first and second reference signals, and forms a plurality of frequency sub-band feedforward signals based on the determined direction of propagation of each of the plurality of frequency sub-band acoustic waves; and
the audio transducer generates the secondary acoustic wave based on the plurality of frequency sub-band feedforward signals.

17. The system of claim 10, wherein the feedforward module forms the feedforward sub-band signal further based on estimated sub-band transfer functions between the listening position and the first and second reference positions, the estimated sub-band transfer functions having corresponding parameters at least comprising an amplitude, at least one of the corresponding parameters being determined as a function of the direction of propagation for each sub-band of the primary acoustic wave.

18. A non-transitory computer readable storage medium having embodied thereon a program, the program being executable by a processor to perform a method for reducing an acoustic energy level at a listening position, the method comprising:
receiving a primary acoustic wave at a first reference position to form a first reference signal;
receiving the primary acoustic wave at a second reference position to form a second reference signal;
separating each of the first reference signal and the second reference signal into a plurality of sub-band signals in the frequency domain;
determining, in the frequency domain, a direction of propagation of the primary acoustic wave for each sub-band of the first reference signal and each sub-band of the second reference signal based on the first and second reference signals;
forming, in the frequency domain, a feedforward sub-band signal based on the determined direction of propagation of the primary acoustic wave; and
generating a secondary acoustic wave based on the feedforward sub-band signal, the secondary acoustic wave adapted to reduce the acoustic energy level at the listening position.

19. The non-transitory computer readable storage medium of claim 18, wherein determining, in the frequency domain, the direction of propagation of the primary acoustic wave is based on at least one of an amplitude difference and a phase difference between the first reference signal and the second reference signal.

20. The non-transitory computer readable storage medium of claim 19, wherein determining, in the frequency domain, the direction of propagation of the primary acoustic wave is based on a time delay estimation between the first reference signal and the second reference signal.

* * * * *